United States Patent [19]

Dahlberg et al.

[11] Patent Number: 5,245,999
[45] Date of Patent: Sep. 21, 1993

[54] METHOD OF ESTABLISHING A FEEDTHROUGH AND A FEEDTHROUGH IN AN IMPLANTABLE APPARATUS FOR STIMULATING LIVING TISSUE

[75] Inventors: Kenneth Dahlberg, Stockholm; Per Jarl, Järfälla, both of Sweden

[73] Assignee: Siemens Aktiengesellschaft, Munich, Fed. Rep. of Germany

[21] Appl. No.: 941,147
[22] PCT Filed: Apr. 16, 1991
[86] PCT No.: PCT/EP91/00720
 § 371 Date: Nov. 12, 1992
 § 102(e) Date: Nov. 12, 1992
[87] PCT Pub. No.: WO91/17792
 PCT Pub. Date: Nov. 28, 1991

[30] Foreign Application Priority Data
 May 15, 1990 [SE] Sweden ............ 9001747

[51] Int. Cl.⁵ ............................................. A61N 1/362
[52] U.S. Cl. ............................................. 609/9
[58] Field of Search ................................. 128/419 P

[56] References Cited
 U.S. PATENT DOCUMENTS

| | | |
|---|---|---|
| 3,735,766 | 5/1973 | Bowers et al. ........ 128/419 P |
| 4,010,759 | 3/1977 | Boer ...................... 128/419 P |
| 4,142,532 | 3/1979 | Ware ..................... 128/419 P |
| 4,301,805 | 11/1981 | Peers-Trevarton et al. ... 128/419 P |
| 4,532,931 | 8/1985 | Mills ..................... 128/419 P |
| 4,712,557 | 12/1987 | Harris ................... 128/419 P |
| 4,715,380 | 12/1987 | Harris ................... 128/419 P |
| 4,898,173 | 2/1990 | Daglow et al. ........ 128/419 P |

FOREIGN PATENT DOCUMENTS
 2055296 3/1981 United Kingdom.

Primary Examiner—William E. Kamm
Assistant Examiner—Scott M. Getzow

[57] ABSTRACT

A common feedthrough for an implantable apparatus for stimulating living tissue, such as a pacemaker, which permits both unipolar and bipolar operation of the pacemaker, is established by a sleeve filled with insulating compound, through which first, second and third conductors proceed. The second conductor and the third conductor are electrically linked to each other at one end, and the third conductor is connected to the sleeve via a joining element. The first conductor is connected to a stimulating pole of the apparatus and to an output terminal at which stimulating pulses are supplied. The free end of the second conductor is connected to an indifferent pole of the apparatus, and the free end of the third conductor is connected to a reference pole of the apparatus. With the conductors connected in this manner, the apparatus can be operated in a unipolar mode. If operation in a bipolar mode is desired, the third conductor is cut outside of the housing.

10 Claims, 2 Drawing Sheets

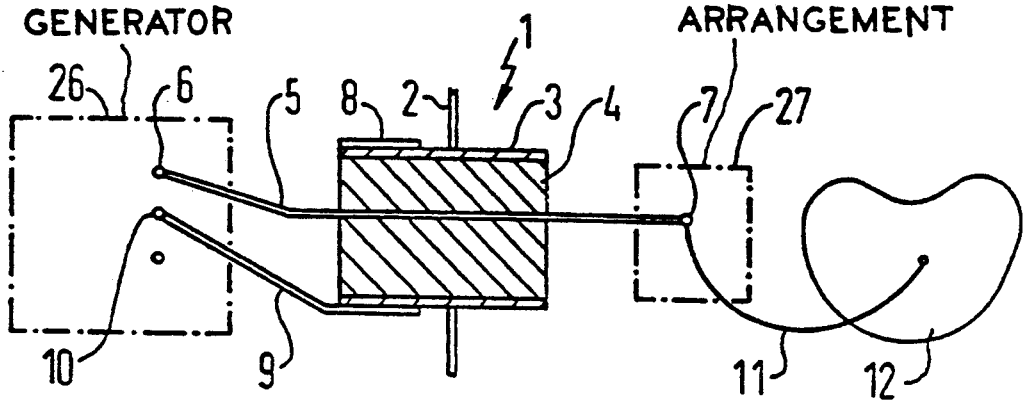
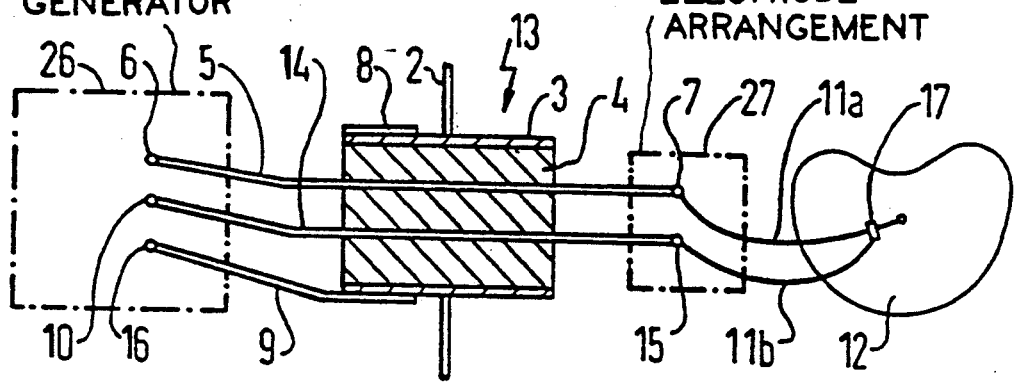
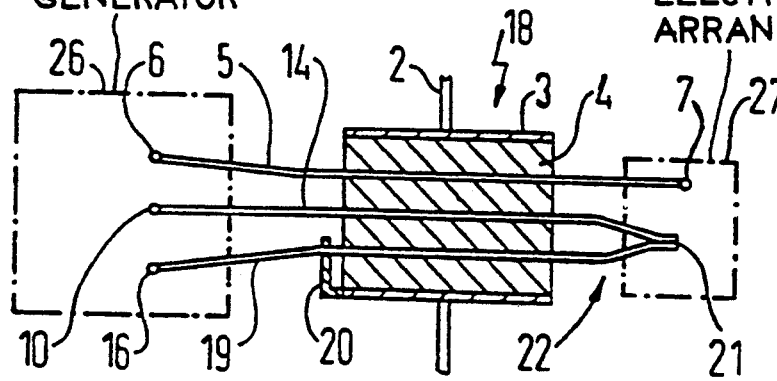

METHOD OF ESTABLISHING A FEEDTHROUGH AND A FEEDTHROUGH IN AN IMPLANTABLE APPARATUS FOR STIMULATING LIVING TISSUE

BACKGROUND OF THE INVENTION

1. Field of the Invention

The invention relates to a method of establishing a feedthrough, and to a feedthrough structure in an implantable apparatus for stimulating living tissue, the feedthrough having the function of connecting an output of a stimulating pulse generator inside a housing of the apparatus to an electrode arrangement outside the housing, of the type wherein a first conductor and a second conductor, both connected to the stimulating pulse generator, are led through the wall of the housing without making electrical contact thereto, a connecting detachable means between the second conductor and the housing is provided, whereby the first conductor is connected to a first terminal of the electrode arrangement and whereby the second conductor is connected to a second terminal of the electrode arrangement and the connecting means is detached when the apparatus is in a bipolar working mode.

2. Description of the Prior Art

It is important for an implantable apparatus for stimulating living tissue, a pacemaker for example, that no body fluids are allowed to permeate the apparatus as this would result in a cessation of the function of the apparatus. Therefore, it is necessary for such apparatuses to be well encapsuled.

A pacemaker basically comprises two units - a stimulating pulse generator and an electrode arrangement. The stimulating pulse generator, whose function is to generate stimulating pulses adapted to optimize a patient's heart function, is well enclosed in a housing. The electrode arrangement, whose function is to lead and deliver the stimulating pulses to the heart, generally comprises a connector and an electrode lead, whose distal end is an electrode tip positioned in the heart and whose proximal end is removably fastened to the connector and at the same time close-fitting. The connector itself is well encapsuled with the exception of openings for the proximal end of the electrode lead and for the connection with the stimulating pulse generator.

It is when the stimulating pulse generator and the connector are to be brought together that a feedthrough is of use. It shall connect the two units electrically and fit closely between them. Such a pacemaker is described in German OS 2914034, for example.

A pacemaker can operate either in a unipolar mode or a bipolar mode. It is known to use identical stimulating pulse generators but different feedthroughs and electrode arrangements for the two operating modes. In the unipolar mode, a stimulating pulse is generated by the stimulating pulse generator and conducted from the stimulating pulse generator through a conductor in the feedthrough to the electrode arrangement and via the electrode arrangement out to the heart. From the heart, the stimulating pulse returns to the stimulating pulse generator via the housing, which is connected to the stimulating pulse generator via the feedthrough. In the bipolar mode, another feedthrough is used, which, in addition to from the above mentioned conductor, also comprises a second conductor to which the stimulating pulse generator and a ring electrode of the electrode arrangement are connected. A stimulating pulse generated by the stimulating pulse generator is conducted, as for the unipolar pacemaker, from the stimulating pulse generator via the feedthrough and the electrode lead to the heart, whereby the stimulating pulse returns to the stimulating pulse generator via the ring electrode.

An embodiment of a known feedthrough for a unipolar connection is shown in FIG. 1 and an embodiment of a known feedthrough for a bipolar connection is shown in FIG. 2.

Since the stimulating pulse generator is identical for both unipolar and bipolar pacemakers, the use of two different type of feedthroughs causes a number of technical production problems.

Two different types of feedthroughs have to be manufactured and stocked, and, furthermore, it will, after the mounting of the feedthroughs to the stimulating pulse generator, be necessary to keep double stores to separate the two types of semi-manufactured pacemakers from each other. The decision whether unipolar or bipolar pacemakers are to be manufactured must be taken at a comparatively early stage of the production, which results in an increased vulnerability to variations in the actual need of the two types of pacemakers.

A feedthrough is disclosed in U.S. Pat. No. 4,301,805 located in a pacemaker and which can be used in both unipolar and bipolar modes. A first conductor is connected to a stimulating pulse generator, led through a housing via a first feedthrough terminal and connected to a first terminal of an electrode arrangement. A second conductor is connected to the stimulating pulse generator, led through the housing via a second feedthrough terminal and connected to a connecting means. The connecting means is a bridging system comprising three contact blocks and a set screw which can connect two blocks to each other. The second conductor is connected to the middle block and the housing and a second terminal of the electrode arrangement are respectively connected to the outer blocks. In the unipolar mode, the set screw connects the second conductor to the housing and in the bipolar working mode, the set screw connects the second conductor to the second terminal.

SUMMARY OF THE INVENTION

An object of the invention is to provide a method to establish a feedthrough, and a feedthrough structure, which can be used in both unipolar and bipolar pacemakers and which is easy to manufacture and easy to mount.

The problem of providing a method to establish a feedthrough is inventively solved, by improving the method as described in the introduction, so that the first conductor and the second conductor are inserted into a sleeve which is filled with an insulating compound, and, for forming the connecting means, the second con is connected to the sleeve by means of a return connector, thereby forming a loop. The sleeve is placed in the wall of the housing, making electrical contact thereto, and the first conductor is connected to a stimulating pole, the second conductor to an indifferent pole and the sleeve to a reference pole of the stimulating pulse generator. For detaching the connecting means the return connector is cut.

The foremost advantage is that this method, in a simple way, allows the use of only one type of feedthrough, provided according to the method, in both unipolar and bipolar pacemakers. All that is needed is to cut the return connector in order to have the feedthrough (and the pacemaker) operating in a bipolar mode. Therefore, it is not necessary to manufacture and store more than one type of feedthrough, which makes the pacemakers identical in all stages of production up to the point where the connector is to be mounted to the stimulating pulse generator and the feedthrough. The vulnerability to variations in the actual need of unipolar and bipolar pacemakers, respectively, is decreased and an increase in efficiently is obtained. All feedthroughs are connected in the same manner to the stimulating pulse circuit thereby reducing the risk of product errors.

The problem of providing a feedthrough structure is inventively solved in a feedthrough in an implantable apparatus for stimulating living tissue, wherein a first conductor and a second conductor are connected to the stimulating pulse generator and led through the wall of the housing without making electrical contact thereto, and wherein a detachable connecting means between the second conductor and the housing is provided. The first conductor is connected to a first terminal of the electrode arrangement and the second conductor is connected to a second terminal of the electrode arrangement. The connecting means is detached when the apparatus is in a bipolar mode. The feedthrough comprises further a sleeve in which the first conductor and the second conductor are inserted with an insulating compound filling the sleeve. A return connector forms the connecting means and is connected to the second conductor and the sleeve, thereby forming a loop. The sleeve is placed in the wall of the housing, making electrical contact thereto. The first conductor is connected to a stimulating pole, the second conductor to an indifference pole and the sleeve to a reference pole of the stimulating pulse generator. For detaching the connecting means, the return connector is cut.

The feedthrough according to the invention can be advantageously improved by the addition of a third conductor, connected to the reference pole of the stimulating pulse generator, is which led through the insulating compound in the sleeve out of the housing where it is connected to the second conductor, thereby forming the loop, with the third conductor being connected to the sleeve by means of a joining element.

The advantage of this embodiment is that when the feedthrough is mounted to the stimulating pulse generator, there is no need for an extra connection to connect the sleeve with the reference pole of the stimulating pulse generator, which simplifies the mounting of the feedthrough. Analogous to the first mentioned embodiment, for the bipolar connection of the electrode arrangement the third conductor is cut outside the housing. In connection therewith, the second conductor and the third conductor can be linked before or after the mounting of the feedthrough to the stimulating pulse generator.

The joining element can be placed outside the housing, in the sleeve or inside the housing. The placing of the joining element outside the housing or inside the housing simplifies the manufacturing process of the feedthrough. It is irrelevant for the function of the feedthrough if one or several joining elements are used.

Another advantage can be obtained for the feedthrough in an embodiment wherein the second conductor and the third conductor are a single conductor, which is bent in the shape of a U, with the bent part disposed outside the housing. A feedthrough is thereby obtained which achieves all that may be required of it to function in accordance with the invention and the feedthrough manufacturing process is simplified as the special step to link the second conductor and the third conductor is omitted.

In the following, the state of the art and embodiments of the feedthrough according to the invention are described in connection with five figures.

DESCRIPTION OF THE DRAWINGS

FIG. 1 shows a unipolar feedthrough according to the state of the art.

FIG. 2 shows a bipolar feedthrough according to the state of the art.

FIG. 3 shows a first embodiment of the feedthrough according to the invention.

DESCRIPTION OF THE PREFERRED EMBODIMENTS

Figure 4:
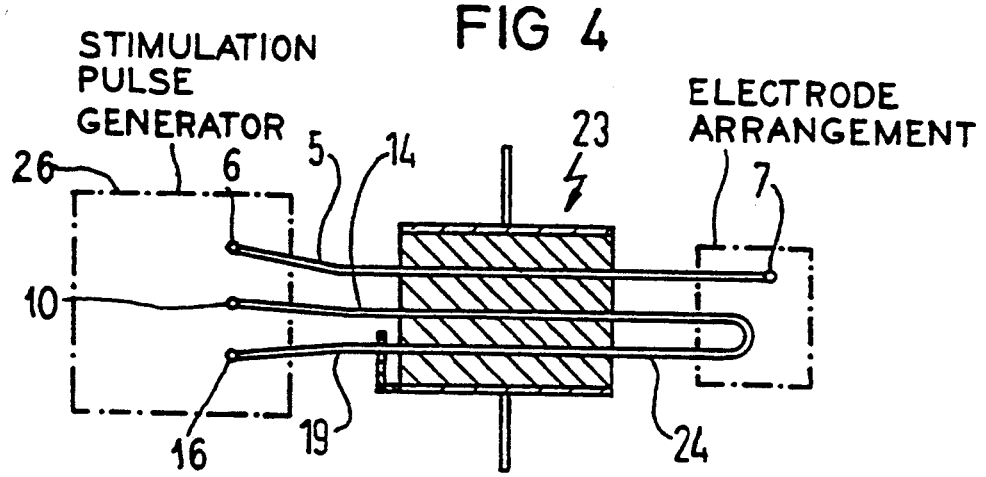
FIG. 4 shows a second embodiment of the feedthrough.

A feedthrough 1 for unipolar connection according to the state of the art is shown in FIG. 1. In a partially shown housing 2 in a pacemaker, a sleeve 3 is placed, which encloses an insulating compound 4 through which a conductor 5 runs. One end of the conductor 5 is connected to a stimulating pole 6 of a stimulating pulse generator 26, indicated with a dash-dotted line, in the pacemaker, and the other end is connected to a corresponding terminal 7 of an electrode arrangement 27, indicated with a dash-dotted line, in the pacemaker. Around the case 3, an annular ring 8 is attached, and on the annular ring 8 is mounted a connecting means 9, which is connected to an indifferent pole 10 of the stimulating pulse generator 26 in the pacemaker. A stimulating pulse from the stimulating pulse generator 26 thereby proceeds from the stimulating pole 6 through the conductor 5 to the electrode arrangement 27 and from there through an electrode lead 11 to a heart 12. Thereafter, the stimulating pulse returns via the housing 2 of the pacemaker to the sleeve 3, the annular ring 8, the connecting means 9 and, finally, to the indifferent pole 10 of the stimulating pulse generator 26.

FIG. 2, similarily, shows a feedthrough 13 for a bipolar connection according to the state of the art. In contrast to the unipolar feedthrough 1, the bipolar feedthrough 13 has a second conductor 14, which runs through the insulating compound 4 in the sleeve 3. This second conductor 14 is connected to the indifferent pole 10 of the stimulating pulse generator 26 and to a corresponding terminal 15 of the electrode arrangement 27. The connecting means 9 is for the bipolar feedthrough 13 connected to a reference pole 16 of the stimulating pulse generator 26 and thereby connects the housing 2 of the pacemaker to the reference pole 16 of the stimulating pulse generator 26 via the sleeve 3, the annular ring 8 and the connecting means 9. A stimulating pulse from the stimulating pulse generator 26 thereby proceeds from the stimulating pole 6 through a first conductor 5 to the electrode arrangement 27 and from there through a first conductor 11a of an electrode lead to the heart 12 and returns via a ring electrode 17 through a second conductor 11b of the electrode lead to the second conductor 14 and the indifferent pole 10 of the stimulating pulse generator 26.

FIG. 3 shows a feedthrough 18, which is adapted to be used for both the unipolar and the bipolar connection in accordance with the invention. As in the known feedthroughs, this feedthrough 18 is has a sleeve 3 filled with an insulating compound 4. A first conductor 5 runs through the insulating compound 4 in the sleeve 3 and one end of said first conductor 5 is connected to the stimulating pole 6 of the stimulating pulse generator 26 in the pacemaker. A second conductor 14 also runs through the insulating compound 4 in the sleeve 3 and is connected with one end to the indifferent pole 10 of the stimulating pulse generator 26. A third conductor 19 likewise runs through the insulating compound 4 in the sleeve 3 and is connected with one end to the reference pole 16 at the stimulating pulse generator 26 and is also, via a joining element 20, connected to the sleeve 3. In FIG. 3, the joining element 20 is placed on the same side of the sleeve 3 as the stimulating pulse generator 26, but might as well be placed on the other side of the sleeve 3 or even inside the sleeve 3. It is also possible to use more than one joining element 20. The second conductor 14 and the third conductor 19 are linked to each other at their free ends 21, outside the housing 2 and thereby form a loop 22. The feedthrough 18 is in FIG. 3 connected unipolarly to the electrode arrangement 27, which only comprises one terminal 7, to which the first conductor 5 is connected. A bipolar connection with the feedthrough 18 is described below in connection with FIG. 5.

FIG. 4 shows a second embodiment of a feedthrough 23 in accordance with the invention In this case, the second conductor 14 and the third conductor 19 are a single conductor 24, which is bent in the middle in a U-shape. Otherwise, the feedthrough 23 is identical with the feedthrough 18 in FIG. 3. When connected unipolarly, which is shown in the figure, only the first conductor 5 is connected to a terminal 7 of the electrode arrangement 27. Bipolar connection of the feedthrough 23 is carried out in a manner analogous with the bipolar connection of the feedthrough 18.

Figure 5:
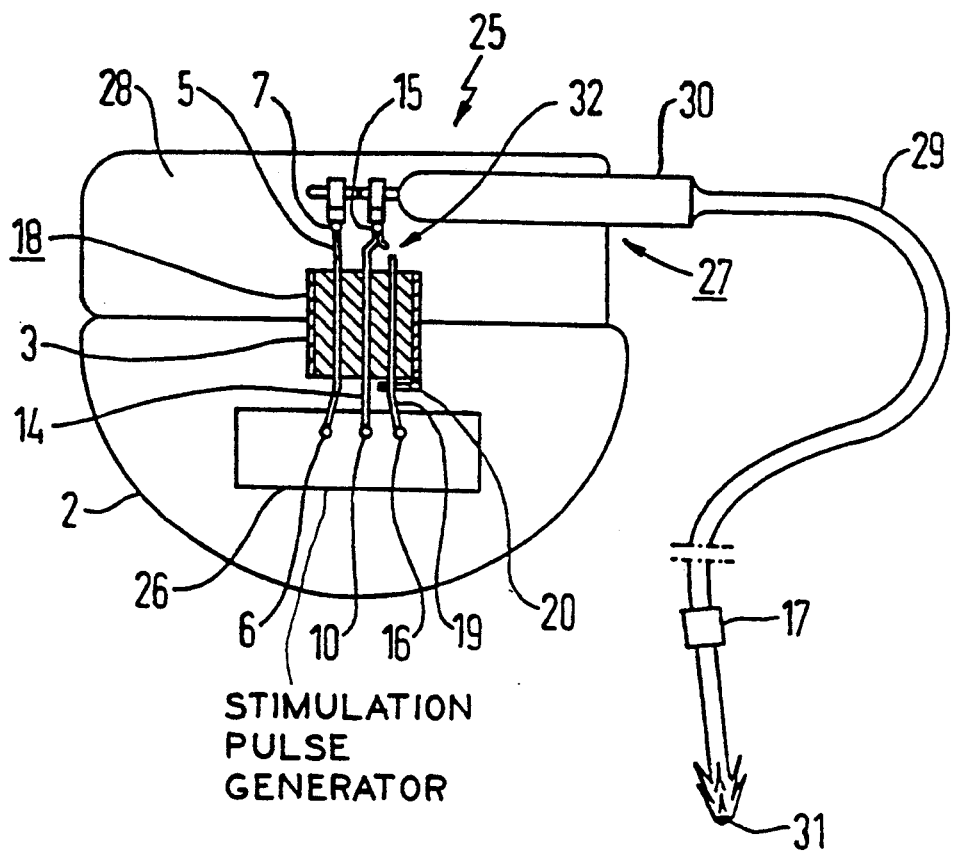
FIG. 5 shows the feedthrough according to FIG. 3 mounted in a bipolar pacemaker.

The positioning, according to the present invention, of the feedthrough 18 in FIG. 3 in a bipolar pacemaker 25, is schematically shown in FIG. 5. In order to emphasize the essential parts of the pacemaker 25, they have been unproportionally altered. The pacemaker 25 basically comprises two parts; the stimulating pulse generator 26 within the housing 2 and the electrode arrangement 27. As described above, the stimulating pulse generator 26 comprises a stimulating pole 6, an indifferent pole 10 and a reference pole 16. The electrode arrangement 27 comprises a conductor 28 and an electrode lead 29. The proximal end 30 of the electrode lead 29 is removably fastened to the connector 28 and in its distal end there is an electrode tip 31 and a ring electrode 17. The feedthrough 18 is placed in the housing 2 of the pacemaker 25 and, through the first conductor 5, connects the stimulating pole 6 to the corresponding terminal 7 of the electrode arrangement 27, which carries stimulating pulses via the electrode lead 29 to the electrode tip 31. The feedthrough 18, through the second conductor 14, also connects the indifferent pole 10 to the corresponding terminal 15 of the electrode arrangement 27 and, via the electrode lead 29, to the ring electrode 17. The third conductor 19 of the feedthrough 18 connects the sleeve 3 to the reference pole 16 via the joining element 20 and is cut at 32, in the part that is outside the housing 2, from its link to the second conductor 14.

Although modifications and changes may be suggested by those skilled in the art, it is the intention of the inventors to embody within the patent warranted hereon all changes and modifications as reasonably and properly come within the scope of their contribution to the art.

We claim:

1. A method of establishing a feedthrough in an implantable apparatus for stimulating living tissue operable in a unipolar or in a bipolar mode, said feedthrough connecting an output of a stimulation pulse generator in a housing of said apparatus to an electrode arrangement outside of said housing, said method comprising the steps of:

running first and second electrical conductors through an electrically conductive sleeve, filled with insulating material, disposed in and making electrical contact with a wall of said housing;

electrically connecting said first conductor to a first terminal of said electrode arrangement and electrically connecting said second conductor to a second terminal of said electrode arrangement;

electrically connecting said second conductor to said sleeve through a return conductor, thereby forming a loop;

connecting said first conductor to a stimulating pole of said pulse generator, connecting said second conductor to an indifferent pole of said pulse generator and connecting said sleeve to a reference pole of said pulse generator; and leaving said return conductor intact for operating said apparatus in said unipolar mode and severing said return conductor for operating said apparatus in said bipolar mode.

2. A method as claimed in claim 1 comprising the additional step of disposing a portion of said return conductor outside of said housing, and wherein the step of severing said return conductor is further defined by severing said return conductor at said portion disposed outside of said housing.

3. In an implantable apparatus for stimulating living tissue operable in a unipolar or in a bipolar mode and having a stimulation pulse generator disposed in a housing and an electrode arrangement disposed outside of said housing, a feedthrough for connecting an output of said stimulation pulse generator to said electrode arrangement comprising:

an electrically conductive sleeve, filled with insulating material, extending through and making electrical contact with a wall of said housing;

a first conductor extending through said insulating material in said sleeve and connected at one end to a stimulating pole of said stimulation pulse generator;

a second electrical conductor extending through said insulating material in said sleeve and connected at one end to an indifferent pole of said stimulation pulse generator;

means for connecting an opposite end of said first conductor to a first terminal of said electrode arrangement;

means for connecting an opposite end of said second conductor to a second terminal of said electrode arrangement;

means for connecting said sleeve to a reference pole of said stimulating pulse generator; and a return connector electrically connecting said second conductor and said sleeve and thereby forming a loop which remains intact for operating said apparatus in said unipolar mode and which is severable for operating said apparatus in said bipolar mode.

4. A feedthrough as claimed in claim 3 wherein said return connector is a third conductor connected to said reference pole of said stimulating pulse generator and extending through said insulating material in said sleeve to a location outside said housing, and connected to said second conductor at said location outside said housing, and a joining element electrically connecting said third conductor to said sleeve.

5. A feedthrough as claimed in claim 4 wherein said third conductor has a region exposed outside of said housing for severing for operating said apparatus in said bipolar mode.

6. A feedthrough as claimed in claim 4 wherein said joining element is disposed outside of said housing.

7. A feedthrough as claimed in claim 4 wherein said joining element is disposed inside said sleeve.

8. A feedthrough as claimed in claim 4 wherein said joining element is disposed inside said housing.

9. A feedthrough as claimed in claim 3 wherein said second and third conductors are electrically connected by a U-shaped bend to form a single conductive element.

10. A feedthrough as claimed in claim 9 wherein said U-shaped bend is disposed outside of said housing.

* * * * *